(12) United States Patent
Sudol

(10) Patent No.: US 12,128,443 B2
(45) Date of Patent: Oct. 29, 2024

(54) IC DIE, PROBE AND ULTRASOUND SYSTEM

(71) Applicant: KONINKLIJKE PHILIPS N.V., Eindhoven (NL)

(72) Inventor: Wojtek Sudol, Andover, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 36 days.

(21) Appl. No.: 17/514,989

(22) Filed: Oct. 29, 2021

(65) Prior Publication Data
US 2022/0048071 A1   Feb. 17, 2022

Related U.S. Application Data

(63) Continuation of application No. 15/757,170, filed as application No. PCT/EP2016/069752 on Aug. 19, 2016, now Pat. No. 11,161,146.

(Continued)

(51) Int. Cl.
*B06B 1/02* (2006.01)
*A61B 8/00* (2006.01)
(Continued)

(52) U.S. Cl.
CPC .............. *B06B 1/0292* (2013.01); *A61B 8/12* (2013.01); *A61B 8/4483* (2013.01); *B06B 1/02* (2013.01);
(Continued)

(58) Field of Classification Search
CPC .......... B06B 1/0292; B06B 1/02; A61B 8/12; A61B 8/4483; B81C 1/00349;
(Continued)

(56) References Cited

U.S. PATENT DOCUMENTS

| 4,841,977 A | 6/1989 | Griffith |
| 6,773,401 B1 * | 8/2004 | Dreschel .............. A61B 8/4483 |
| | | 600/459 |

(Continued)

FOREIGN PATENT DOCUMENTS

| JP | 2002110902 A | 4/2002 |
| JP | 2004228236 A | 8/2004 |

(Continued)

OTHER PUBLICATIONS

Wygant, et al., "An Integrated Circuit With Transmit Beamforming Flip-Chip Bonded to a 2-D CMUT Array for 3-D Ultrasound Imaging", IEEE Transactions on Ultrasounds, Ferroelectrics, and Frequency Control, vol. 56, No. 10, Oct. 2009, pp. 2145-2156.

(Continued)

Primary Examiner — Sanjay Cattungal

(57) ABSTRACT

An integrated circuit die is disclosed that comprises a substrate defining a plurality of circuit elements; a sensor region on the substrate, the sensor region comprising a layer stack defining a plurality of CMUT (capacitive micromachined ultrasound transducer) cells; and an interposer region on the substrate adjacent to the sensor region. The interposer region comprises a further layer stack including conductive connections to the circuit elements and the CMUT cells, the conductive connections connected to a plurality of conductive contact regions on an upper surface of the interposer region, the conductive contact regions including external contacts for contacting the integrated circuit die to a connection cable and mounting pads for mounting a passive component on the upper surface. A probe including such an integrated circuit die an ultrasound system including such a probe are also disclosed.

12 Claims, 6 Drawing Sheets

Related U.S. Application Data

(60) Provisional application No. 62/213,811, filed on Sep. 3, 2015.

(51) Int. Cl.
| | | |
|---|---|---|
| *A61B 8/12* | (2006.01) | |
| *B81C 1/00* | (2006.01) | |
| *H01L 23/00* | (2006.01) | |
| *H01R 9/05* | (2006.01) | |
| *H01R 12/62* | (2011.01) | |
| *H01R 43/20* | (2006.01) | |
| *H05K 3/34* | (2006.01) | |

(52) U.S. Cl.
CPC .......... *B81C 1/00349* (2013.01); *H01L 24/46* (2013.01); *H01R 9/0515* (2013.01); *H01R 12/62* (2013.01); *H01R 43/205* (2013.01); *H05K 3/3421* (2013.01); *H05K 2201/09409* (2013.01); *H05K 2201/10356* (2013.01); *Y02P 70/50* (2015.11)

(58) Field of Classification Search
CPC .......... H01L 24/46; H01L 2924/19105; H01R 9/0515; H01R 12/62; H01R 43/205; H05K 3/3421; H05K 2201/09409; H05K 2201/10356; Y02P 70/50
See application file for complete search history.

(56) References Cited

U.S. PATENT DOCUMENTS

| | | | | |
|---|---|---|---|---|
| 10,293,374 | B2* | 5/2019 | Torashima | G01N 29/2418 |
| 2005/0121734 | A1* | 6/2005 | Degertekin | B06B 1/0292 |
| | | | | 438/48 |
| 2007/0293762 | A1* | 12/2007 | Sawada | B06B 1/0633 |
| | | | | 600/459 |
| 2008/0269614 | A1* | 10/2008 | Adachi | G01N 29/2406 |
| | | | | 310/317 |
| 2010/0251823 | A1* | 10/2010 | Adachi | A61B 8/4483 |
| | | | | 73/606 |
| 2010/0255623 | A1* | 10/2010 | Huang | B06B 1/0292 |
| | | | | 257/E21.532 |
| 2011/0244723 | A1 | 10/2011 | Kojima | |
| 2013/0128702 | A1 | 5/2013 | Degertekin | |
| 2013/0261467 | A1* | 10/2013 | Dausch | B06B 1/0622 |
| | | | | 29/25.35 |
| 2013/0267853 | A1* | 10/2013 | Dausch | A61B 8/445 |
| | | | | 600/459 |
| 2014/0005521 | A1* | 1/2014 | Kohler | A61B 6/4057 |
| | | | | 601/3 |
| 2014/0114195 | A1 | 4/2014 | Inui | |
| 2014/0180072 | A1* | 6/2014 | Davies | A61B 6/12 |
| | | | | 600/424 |
| 2014/0180273 | A1* | 6/2014 | Nair | A61B 8/0891 |
| | | | | 606/34 |
| 2014/0184026 | A1 | 7/2014 | Reiter | |
| 2015/0032002 | A1 | 1/2015 | Rothberg | |
| 2015/0305710 | A1* | 10/2015 | Stigall | A61B 8/0891 |
| | | | | 600/424 |
| 2017/0326589 | A1* | 11/2017 | Sudol | H03H 3/0072 |

FOREIGN PATENT DOCUMENTS

| | | |
|---|---|---|
| JP | 2013150198 A | 8/2013 |
| WO | 2014014968 A1 | 1/2014 |

OTHER PUBLICATIONS

LM2704 Micropower Step0up DC/DC Converter with 550mAPEAK Current Limit, Texas Instruments, 2002.
DRAM, 1996, pp. 1106-1113.
Ergun, Arif Sanli et al "Capacitive Micromachined Ultrasonic Transducers: Fabrication Technology", IEEE Transactions on Ultrasonics, Ferroelectrics, and Frequency Control, vol. 52, No. 12, Dec. 2005.

* cited by examiner

IC DIE, PROBE AND ULTRASOUND SYSTEM

PRIORITY

This application is a continuation of U.S. patent application Ser. No. 15/757,170 (now U.S. Pat. No. 11,161,146) filed on Mar. 2, 2018. That application is the U.S. National Phase application under 35 U.S.C. § 371 of International Application No. PCT/EP2016/069752, filed on Aug. 19, 2016, which claims the benefit to both U.S. Provisional Application Ser. No. 62/213,811, filed Sep. 3, 2015, and to European Application Serial No. 15198399.6, filed Dec. 8, 2015. All of these applications are hereby incorporated by reference herein.

FIELD OF THE INVENTION

The present invention relates to an IC die comprising a substrate defining a plurality of circuit elements and a plurality of CMUT (capacitive micromachined ultrasound transducer) cells on the substrate.

The present invention further relates to a probe including such an IC die.

The present invention yet further relates to an ultrasound system including such a probe.

BACKGROUND OF THE INVENTION

IC dies including ultrasound sensing capabilities, e.g. ultrasonic transducer chips, are increasingly used as a sensing tip of an ultrasound probe such as an ultrasound catheter. The ultrasound sensing capabilities may for instance be provided by a plurality of transducer elements in a main surface of the ultrasonic transducer chip, e.g. to provide a forward looking or sideward looking ultrasound probe. Popular technologies to implement the transducer elements include piezoelectric transducer elements formed of materials such as lead zirconate titanate (PZT) or polyvinylidene-fluoride (PVDF) and capacitive micro-machined ultrasonic transducer (CMUT) elements. An ultrasonic transducer chip based on such CMUT elements is sometimes referred to as a CMUT device.

CMUT devices are becoming increasingly popular because CMUT devices can offer excellent bandwidth and acoustic impedance characteristics, which makes them the preferable over e.g. piezoelectric transducers. Vibration of the CMUT membrane can be triggered by applying pressure (for example using ultrasound) or can be induced electrically. Electrical connection to the CMUT device, often by means of an integrated circuit (IC) such as an application specific integrated circuit (ASIC) facilitates both transmission and reception modes of the device. In reception mode, changes in the membrane position cause changes in electrical capacitance, which can be registered electronically. In transmission mode, applying an electrical signal causes vibration of the membrane. A pressure causes a deflection of the membrane that is electronically sensed as a change of capacitance. A pressure reading can then be derived.

Miniaturization is a particular challenge when developing ultrasound probes. In particular, where such probes are to be used for advanced diagnostic purposes, e.g. cardiac investigations and surgery, such probes must be as small as possible to allow the probe to enter the body part of interest. At the same time, the ultrasound probe should be rigid, e.g. when used as the tip of a catheter to allow the probe to be guided into the body part of interest in a controlled manner. These requirements are difficult to reconcile with the desire to include significant signal processing capability at the probe.

Specifically, it may be desirable to include active components, e.g. IC dies such as application specific integrated circuits (ASICs) at the probe tip to provide the ultrasound transducer cells with control signals and to process the response signals, as well as passive components such as decoupling capacitors that for instance protect the various circuits from fluctuations in the supply voltage, e.g. supply bounce, which can be caused by the power consumption behaviour some of the components, in particular the ASICs. Such passive components, e.g. discrete capacitors or resistors, are typically mounted on a printed circuit board or interposer. An example of such an arrangement is schematically depicted in FIG. 1, which shows a forward-looking ultrasound probe 100, here a catheter, comprising a body 200 onto which an IC die 1 comprising CMUT cells is mounted. The body 200 may define a flexible tip of the ultrasound probe 100. The annular section 202 of the body 200 houses the IC die 1 whereas the arcuate section 204 of the body 200 houses part of a PCB 300 having board contacts 310 that are conductively coupled to conductive tracks of the body 200 by interconnections 240, e.g. bond wires. The conductive tracks typically comprise portions that act as electrically conductive contact surfaces for forming the interconnections with the PCB contacts 310.

The PCB 300 is typically connected at a section opposite the body 200 to conductive wires 410, e.g. a coaxial cable, which conductive wires 410 for instance may connect the PCB 300 to an external data processor and/or control unit (not shown). The conductive wires 410, e.g. the coaxial cable, may be housed in a main body 400, e.g. a fibre or the like, onto which the tip of the ultrasound probe 100 is mounted. The PCB 300 may comprise circuitry 320, e.g. the aforementioned passive components as well as some signal processing circuitry, such as for instance a microbeam former. The tip of the ultrasound probe 100 may be covered in an electrically insulating protective material, e.g. a suitable resin, to protect the PCB 300 and the conductive parts of the tip to exposure to external environments, e.g. (corrosive) bodily fluids during internal use of the ultrasound probe 100. This arrangement is relatively bulky.

SUMMARY OF THE INVENTION

The present invention seeks to provide an integrated circuit die facilitating a more compact ultrasound transducer probe.

The present invention further seeks to provide a probe comprising such an integrated circuit die.

The present invention further seeks to provide an ultrasound system including such a probe.

According to an aspect, there is provided an integrated circuit die comprising a substrate defining a plurality of circuit elements; a sensor region on the substrate, the sensor region comprising a layer stack defining a plurality of ultrasound transducer cells; and an interposer region on the substrate adjacent to the sensor region, the interposer region comprising a further layer stack including conductive connections to the circuit elements and the ultrasound transducer cells, the conductive connections connected to a plurality of conductive contact regions on an upper surface of the interposer region, the conductive contact regions including external contacts for contacting the integrated circuit die to a connection cable and mounting pads for mounting a passive component on the upper surface.

The present invention is based on the insight that the IC die such as an ASIC may be extended to comprise interposer functionality by partitioning the upper region of the IC die into a sensor region comprising ultrasound transducer cells, e.g. CMUT cells or piezoelectric transducer elements, and an interposer region providing the interconnections to the IC die as well as mounting pads for mounting passive components such as resistors and decoupling capacitors on the IC die. In this manner, a particularly compact arrangement is provided as the need for a separate interposer is avoided.

The integrated circuit die may further comprise a metallization stack in between the substrate and the sensor and interposer regions, such that the sensor and interposer regions are formed on top of the metallization stack.

At least one passive component may be mounted on the mounting pads on said upper surface. The at least one passive component may comprise a decoupling or by-pass capacitor, which has the advantage that the decoupling or by-pass capacitor is located in close vicinity to the circuit components of the IC die, thereby minimizing parasitic resistance and capacitance.

In an embodiment, the interposer region is recessed relative to the sensor region. The provision of an interposer region with reduced thickness reduces the aspect ratio of the conductive conduits from the upper surface of the interposer region to the circuit elements in the substrate or to the metallization stack on top of these circuit elements, which may improve the reliability and/or quality of these conductive conduits.

The external contacts may comprise a first external contact region along an edge of the upper surface opposite a boundary between the sensor region and the interposer region; and a second external contact region in between the first external contact region and said boundary in order to increase the contact density in a compact manner. The first external contact region may comprise at least one external contact for grounding the integrated circuit die and the second external contact region comprises an array of external contacts for contacting the integrated circuit die to an external cable.

In an embodiment, the second external contact region comprises a further array of external contacts for contacting the integrated circuit die to the external cable, the further array positioned between the first array and said boundary. In this manner, a large number of contacts may be formed with the IC die, for instance by contacting the IC die with a connection cable having layers of connection wires, with different layers connecting to different external contact arrays of the IC die, thus providing a particularly compact connection scheme.

In an embodiment, the external contacts comprise an array of external contacts, the upper surface further comprising an array of alignment members in between the array of external contacts and said boundary, wherein each external contact of said array of external contacts is positioned in between a pair of neighbouring alignment members in said array of alignment members. This facilitates connecting the IC die to a connection cable comprising connection wires, as the connection wires may be guided onto the external contacts by the alignment members. To this end, the alignment members preferably are protrusions extending from the upper surface, which protrusions preferably are made from an electrically insulating material, e.g. a dielectric material used to form at least part of the membrane in case of CMUT ultrasound transducer cells.

The contact regions may be plated with at least one of gold and nickel in order to protect the contact regions from corrosion and to improve bonding of a connection cable to the external contacts and/or bonding of a passive component to the mounting pads.

According to another aspect, there is provided a probe comprising the integrated circuit die of any of the above embodiments with at least one passive component mounted on the mounting pads; and a connection cable mounted on the external contacts. Such a probe is particularly compact and therefore ideally suited for use in application domains where a small form factor of such an ultrasound probe is required.

The integrated circuit die and at least a part of connection cable mounted on the external contacts may be encapsulated in a resin encapsulation in order to protect the integrated circuit die and its connection to the connection cable from accidental damage.

The resin encapsulation may comprise a recessed portion over the sensor region to reduce the amount of resin ultrasound waves generated or received by the sensor region have to travel through, thereby improving the sensitivity of the probe.

According to yet another aspect, there is provided an ultrasound system comprising the probe of any of the above embodiments and a control interface connected to the probe by the connection cable. The ultrasound system may be an ultrasound diagnostic imaging system or an ultrasound therapeutic system.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
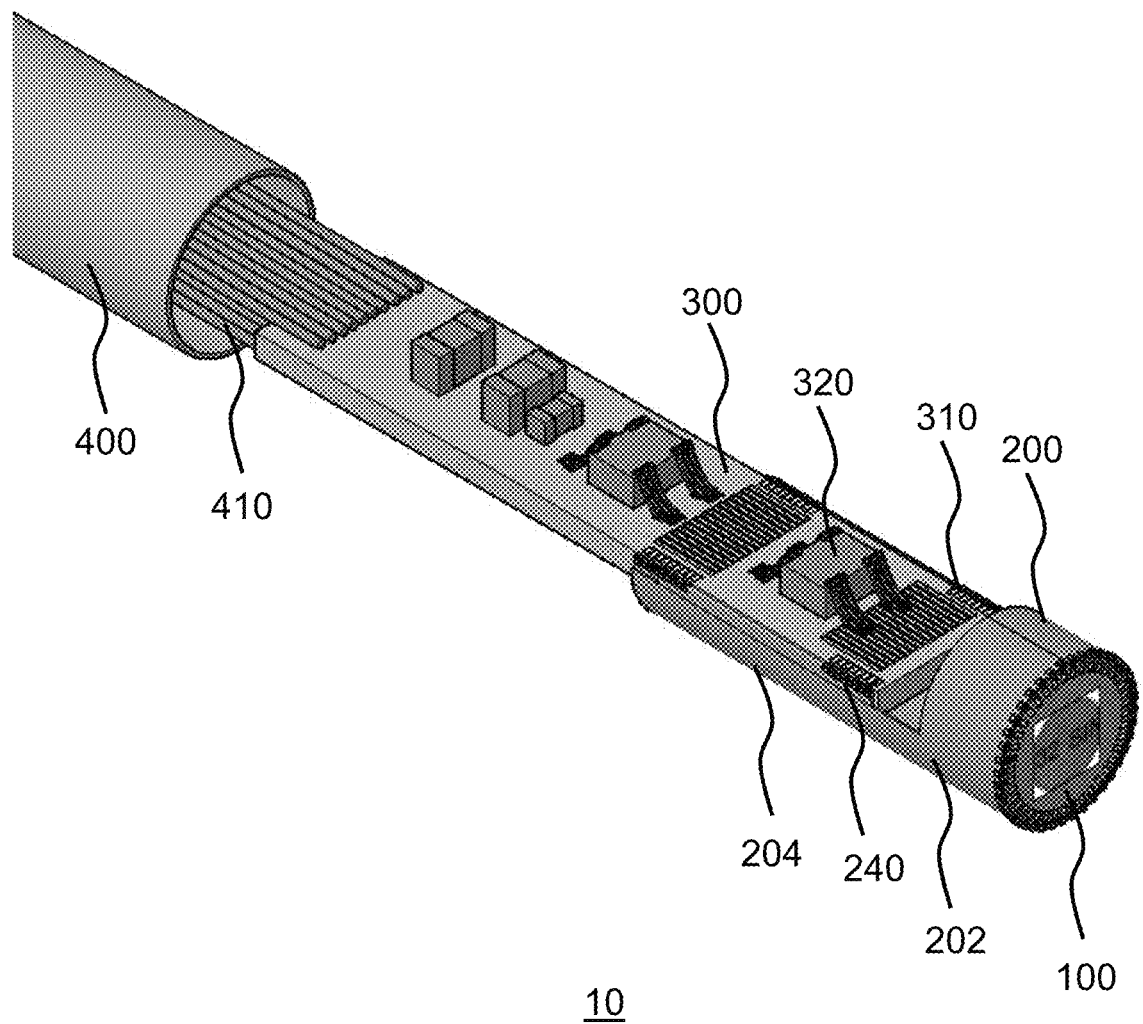
FIG. 1 schematically depicts a prior art catheter probe arrangement.

It should be understood that the Figures are merely schematic and are not drawn to scale. It should also be understood that the same reference numerals are used throughout the Figures to indicate the same or similar parts.

Figure 2:
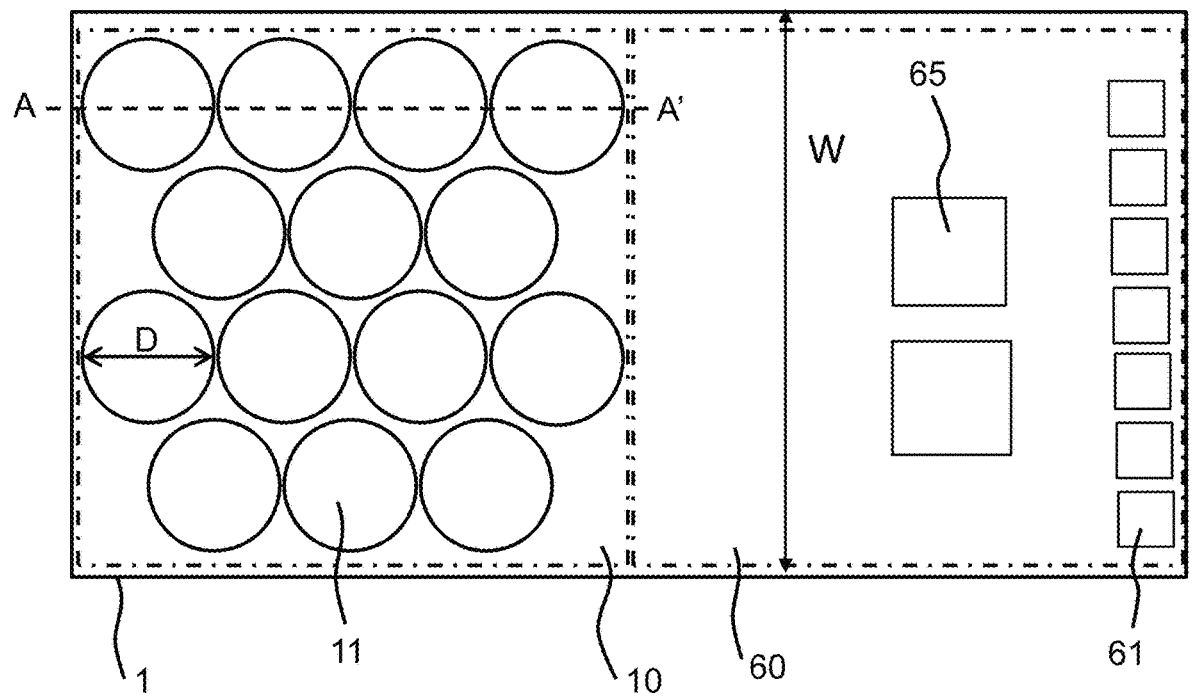
FIG. 2 schematically depicts a top view of a CMUT IC die according to an embodiment.
Figure 3:
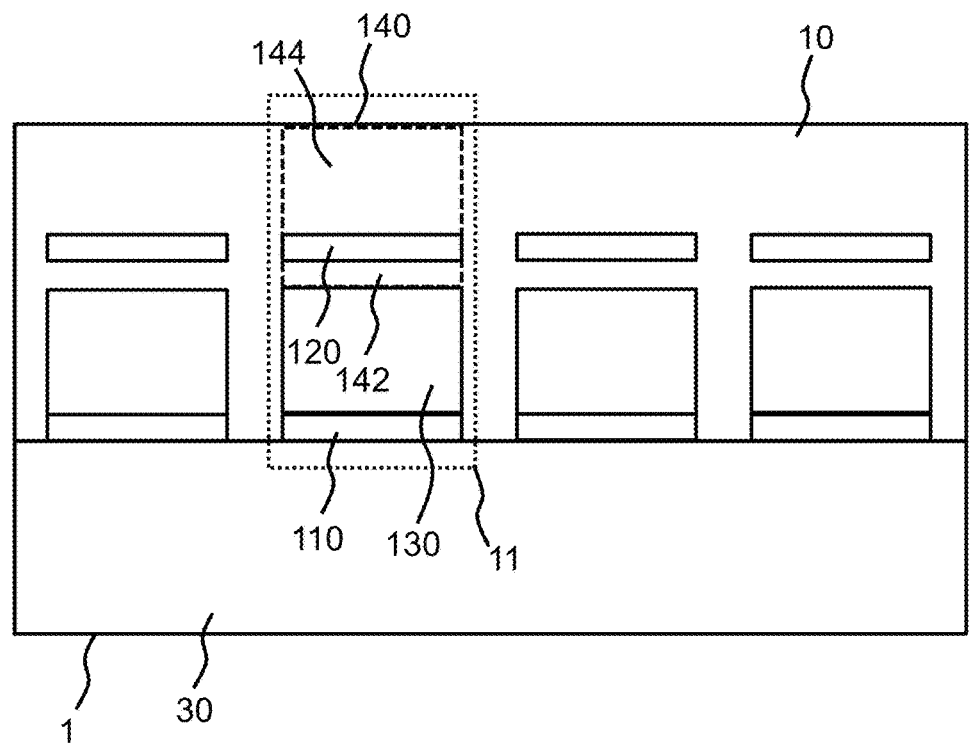
FIG. 3 schematically depicts a cross-section of the CMUT IC die of FIG. 2 along line A-A'.

FIG. 2 schematically depicts a top view and FIG. 3 schematically depicts a cross-section along the line A-A' in FIG. 2 of an IC die 1 such as an ASIC according to an embodiment. The IC die 1 comprises a plurality of ultrasound transducer cells 100, here CMUT cells each having a membrane diameter D in a CMUT region 10 of the IC die 1 and an integrated interposer region 60 adjacent to the CMUT region 10 comprising a plurality of external contacts 61 for connecting the IC die 1 to a coaxial cable and a plurality of mounting pads 65 onto which discrete compounds such as resistors and decoupling or bypass capacitors may be mounted. It should however be understood that any suitable type of ultrasound transducer cells 100, e.g. piezo-electric transducer elements, may be deployed instead of the CMUT cells, although for the sake of brevity in the remainder of this description reference will be made to CMUT cells 100 by way of non-limiting example only.

The external contacts 61 may include contacts to the respective electrodes of the CMUT cells 100 and other circuits included in the IC die 1, such as signal processing circuitry for generating and/or processing signals provided to or received from the CMUT cells 100. The external contacts 61 may further power terminals, which for instance may be conductively coupled to the mounting pads 65 such that a power supplied to the IC die 1 is routed through a passive component mounted on the mounting pads 65 before being supplied to the internals of the IC die 1, for example to protect the internals of the IC die 1 from spikes or the like in the power supply. In an embodiment, the external contacts 61 further comprise thermistor contacts for contacting an external device to a thermistor (not shown) in the interposer region 60, for instance to facilitate monitoring of an ambient temperature to which the IC die 1 is exposed.

The CMUT cells 100 for example may be mounted on top of the metallization stack of the IC die 1 that provides the interconnection between the active components or circuitry formed in the substrate of the IC die 1. In an embodiment, the metallization stack further provides the interconnections to the external contacts 61 and landing pads, for instance through the provisions of vias that extend from the metallization stack to the external contacts 61 and mounting pads through the various (electrically insulating) layers over the metallization stack including a passivation layer stack that may be present in between the metallization stack and the CMUT region 10 and integrated interposer region 60 respectively.

The external contacts 61 and mounting pads 65 are typically made of a conductive material, for instance a metal such as copper, aluminium or a copper/aluminium alloy. Other suitable electrically conductive materials will be immediately apparent to the skilled person. The electrically conductive materials, e.g. metals or metal alloys, preferably are materials that are integrated in an existing semiconductor manufacturing process, e.g. CMOS, such that the process does not require extensive redesign to facilitate the provision of the external contacts 61 and mounting pads 65.

In an embodiment, the external contacts 61 and mounting pads 65 may be plated to protect them from corrosion and/or to improve their suitability for a solder process in which a connection wire or a passive component is soldered onto the contacts. The external contacts 61 and mounting pads 65 may be plated using any suitable plating technique such as electroplating or electroless plating. In an embodiment, the plating is nickel plating. In an alternative embodiment, the plating comprises a nickel barrier layer on the contacts and a gold layer on the nickel barrier layer, e.g. formed through ENIG plating techniques. The gold layer may be separated from the nickel barrier layer by a palladium layer. Such a layer stack for instance may be formed through ENEPIG plating techniques. Other suitable plating arrangements will be immediately apparent to the skilled person. The thickness of the plating may be chosen in accordance with the connection technique used to connect a connection cable to the external contacts 61. For example, where such a connection cable is soldered to the external contacts 61, the overall thickness of the plating may be less than 1 μm, whereas where such a connection cable is welded to the external contacts 61, the overall thickness of the plating may exceed 1 μm.

In an example embodiment, each CMUT cell 100 comprises a first electrode 110 separated from a second electrode 120 by a cavity 130, as shown in FIG. 3, which schematically depicts the cross section along the line A-A' in FIG. 2. The second electrode 120 is typically embedded in a membrane 140 made of one or more electrically insulating or dielectric layers, which may extend over the integrated interposer region 20. In some designs, the second electrode 120 may be embedded in the membrane 140, i.e. sandwiched in between a relatively thin dielectric layer portion 142 and a relatively thick dielectric layer portion 144 from the cavity 130 to prevent a short circuit between the first electrode 110 and the second electrode 120 upon deformation of the membrane 140 including the second electrode 120 towards the first electrode 110.

The membrane 140 may have any suitable thickness. Some CMUT designs have membrane 140 layer thicknesses in the order of 1-2 micron, which can be processed with common fabrication methods such as plasma-enhanced chemical vapor deposition (PECVD). However, where the CMUT cells 100 are required to operate at a low frequency, the membrane diameter D may need to be in excess of 100 micron, which can result in the thickness of the membrane 140 becoming larger than 3 micron, in particular when the substrate 30 on which the CMUT cells 100 are formed comprises planarization and/or encapsulation layers. Such additional layers can add another 2-3 micron to the overall thickness of the dielectric layer stack.

It should be understood that this is merely an example embodiment of the CMUT cells 100. The design of the CMUT cells 100 is not particularly relevant to the present invention, and any suitable design of the cells may be contemplated; for example, 3-electrode CMUT cells 100 in which an intermediate electrode is located between the bottom electrode 110 and the cavity 130 are equally feasible. Such 3-electrode CMUT cells for instance may be contemplated to provide a stimulus and a bias voltage through separate electrodes, e.g. to reduce the risk of membrane sticking to the bottom of the CMUT cell.

Figure 4:
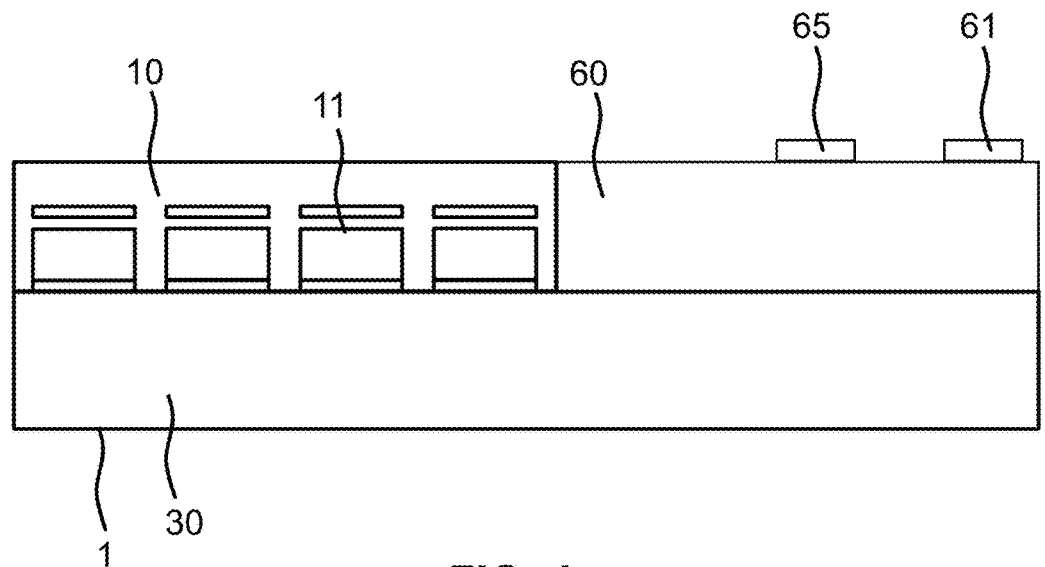
FIG. 4 schematically depicts another cross-section of the CMUT IC die of FIG. 2.

FIG. 4 schematically depicts a cross section of the full width of the IC die 1 including the sensor region 10 with CMUT cells 11 and the interposer region 60 adjacent to the sensor region 10, with both regions formed on top of the substrate 30 of the IC die 1. The substrate 30 may be any suitable type of substrate, such as a silicon substrate, a silicon on insulator substrate, a silicon germanium substrate, and so on. The substrate 30 may carry a metallization stack (not shown) that provides interconnections between the circuit elements in the substrate 30, with the sensor region 10 and the interposer region 60 separated from the metallization stack by a passivation layer (stack) or similar located in between the regions 10, 60 and the metallization stack.

The sensor region 10 and the interposer region 60 are typically simultaneously formed, that is, the various layers deposited to form the CMUT cells 11 in the sensor region 10 may be extended over the substrate 30 to form the interposer region 60 by suitable patterning of these layers as will be well-known per se to the skilled person. For example, a metal layer with optional barrier layer may be formed on the substrate 30 (or metallization stack) in any suitable manner, e.g. through sputtering, after which the layers are etched, e.g. dry-etched, to form the bottom electrode 110 optionally covered by a barrier layer in the sensor region 10 and to form interconnection structures in the interposer region 60.

A dielectric layer may be formed over the bottom electrode 110 and the interconnection structures, e.g. through a deposition process such as PECVD. Suitable materials for the dielectric layer include but are not limited to SiO2, preferably formed through a TEOS deposition process, oxide-nitride-oxide (ONO), high-k dielectrics and oxides such as aluminium oxide, various grades including silane, SiH4-based PECVD SiO2, and so on. SiO2 formed through a PECVD deposition process of TEOS is particularly preferred.

A sacrificial material is deposited over the resulting structure and subsequently patterned to define the outline of the cavity 130 to be formed, after which in an optional step a further dielectric layer may be formed over the resulting structure, e.g. through deposition such as PECVD. Suitable sacrificial materials include but are not limited to metals, metal alloys, layer stacks including a metal layer with a capping layer, amorphous silicon and so on. Aluminium alloys such as Al/Nd and Al/Mo are particularly suitable. Suitable materials for the further dielectric layer include but are not limited to SiO2, preferably formed through a TEOS deposition process, oxide-nitride-oxide (ONO), high-k dielectrics and oxides such as aluminium oxide, various grades including silane, SiH4-based PECVD SiO2, and so on. SiO2 formed through a PECVD deposition process of TEOS is particularly preferred. Trenches such as vias may be formed through the dielectric layers in the interposer region 60 and filled with a conductive material to provide conductive connections to the interconnection structures.

An optional further barrier layer and further metal layer are subsequently formed or deposited in any suitable manner, e.g. through sputtering, after which the layers are patterned, e.g. (dry-)etched, to form the upper electrode 120 optionally separated from the underlying structure by further barrier layer in the sensor region 10, with the patterned further metal layer forming further interconnection structures in the interposer region 60. The further interconnection structures may be connected to the interconnection structures by the previously mentioned trenches or vias.

Next, the flexible membrane 144, e.g. a membrane formed of one or more high breakdown materials such as silicon nitride or any other suitable material, is formed over the upper electrode 120 and underlying structure, e.g. through any suitable deposition technique, which high breakdown material layers may extend over the interposer region 60 to provide electrical insulation for the (further) interconnection structures in the interposer region 60. A vent hole or chimney (not shown) is formed through the flexible membrane 144 through which the sacrificial material is removed, thereby forming the cavity 130, after which the vent hole or chimney is sealed in any suitable manner, as is known per se. For example, the sealing process may be carried out under vacuum conditions using PECVD deposition or sputtering, in which a sealing material, e.g. SiN, TEOS, an oxide-nitride-oxide material stack, metal, and so on, is deposited in the vent hole to seal it. As will be readily understood by the skilled person, the pressure difference between the pressure inside the cavity 130 and the external pressure will determine the shape of the flexible membrane 144 in air. Further trenches or vias may be formed through the high breakdown materials in the interposer region 60 and filled with a conductive material to provide conductive connections to the further interconnection structures.

In an embodiment, part of the high breakdown material layers in the interposer region 60 may be removed to reduce the thickness of the dielectric layer stack in the interposer region 60 prior to forming the further trenches or vias to reduce the aspect ratio of these trenches or vias. This is to avoid partial filling only of the trenches or vias with a conductive material, which can become an issue if the aspect ratio of the trenches or vias becomes too high, i.e. trenches or vias having a much larger height than width.

The electric contacts 61 and mounting pads 65 are subsequently formed on the upper surface of the interposer region 60 using any suitable deposition technique to facilitate the IC die 1 being suitable for connecting to a connection cable and for receiving one or more passive components on the mounting pads 65. The electric contacts 61 and mounting pads 65 are typically connected to the further trenches or vias.

At this point, it is noted that the above-mentioned in process is one of many straightforward alternatives of such a manufacturing process as will be immediately apparent to the skilled person. Any of these alternatives may be used to produce an IC die 1 according to an embodiment of the present invention.

Figure 5:
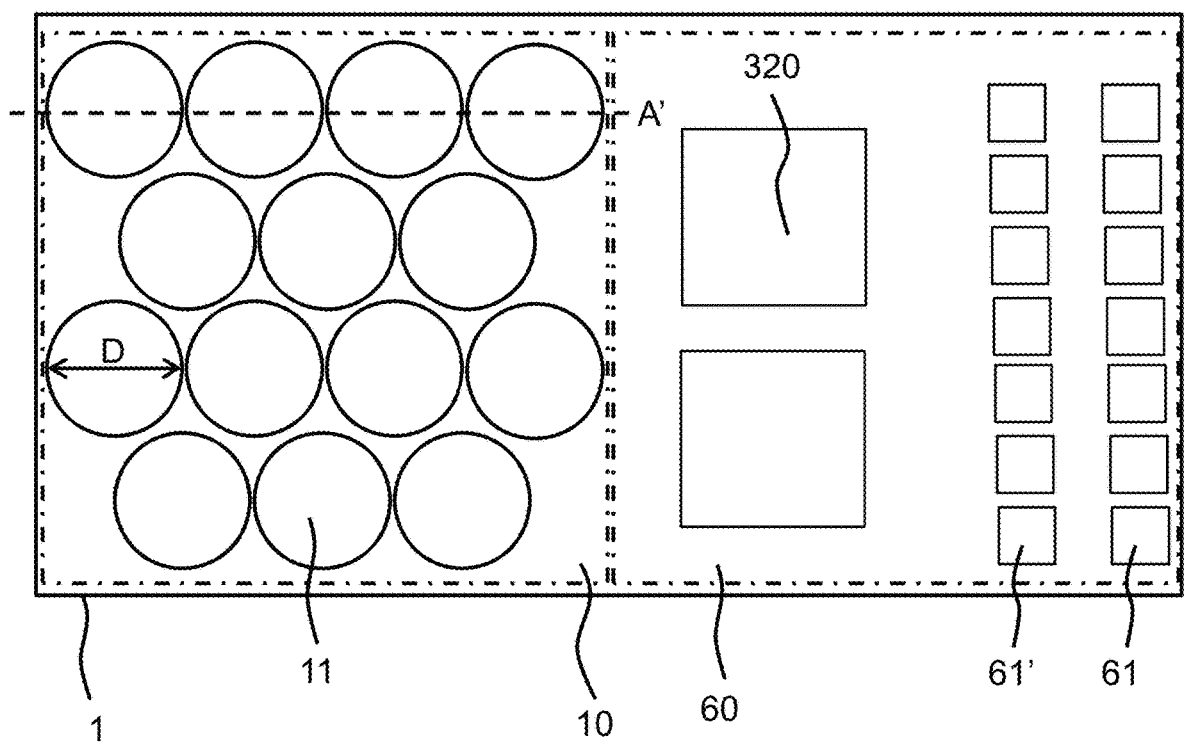
FIG. 5 schematically depicts a top view of a CMUT IC die according to another embodiment.

In FIG. 2, a single row or array of external contacts 61 is shown along an edge of the interposer region 60 opposite the boundary between the sensor region 10 and the interposer region 60. Such a single array of external contacts 61 for instance may be appropriate where only a relatively small number of (signal) channels, e.g. 8 channels, are incorporated in the IC die 1. FIG. 5 schematically depicts a top view of an IC die 1 comprising multiple rows or arrays of external contacts 61 including a first array of external contacts 61 along the edge of the interposer region 60 opposite this boundary and a second array of external contacts 61 in between the first array and the boundary. This for instance facilitates the connection of a larger number of signal channels to the IC die 1, e.g. up to 120 channels. In FIG. 5, a discrete passive component 320 is mounted on one or more mounting pads 65, such as a decoupling or bypass capacitor, resistor or the like.

Figure 6:
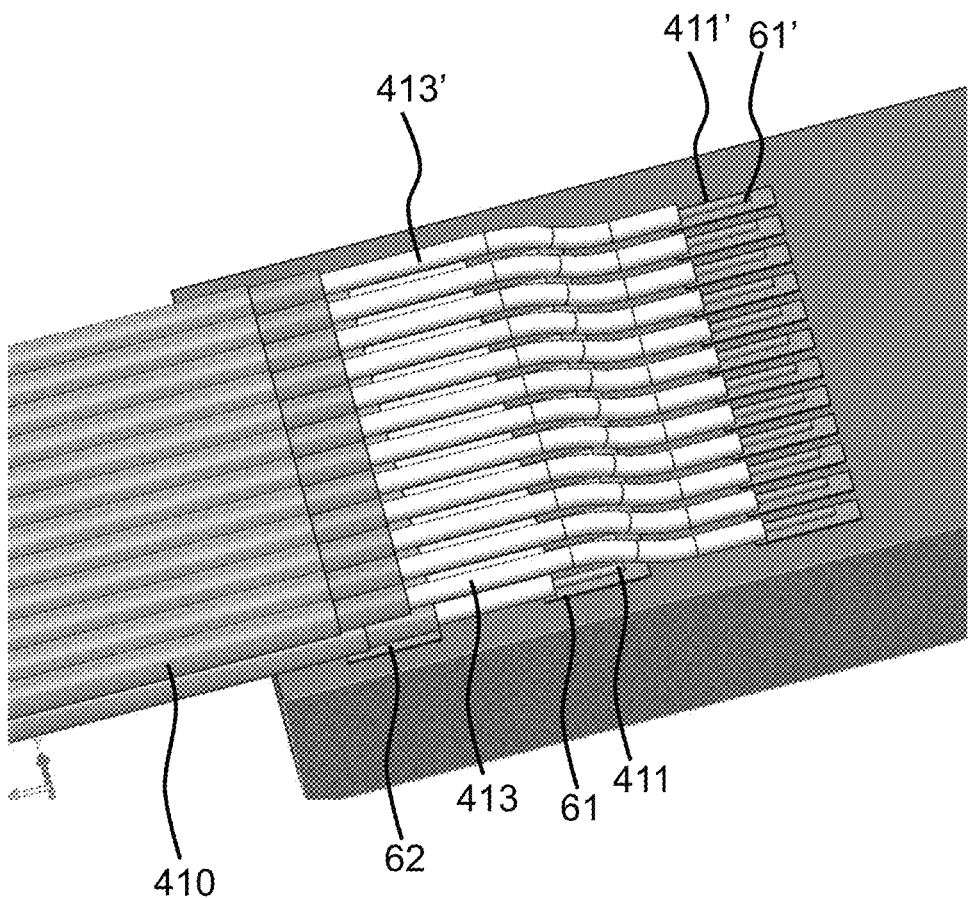
FIG. 6 schematically depicts a connection between a coaxial cable and part of the CMUT IC die of FIG. 5.

Such interconnections for instance may be provided using a cable arrangement, which may comprise a coaxial cable, in which layers of wires are provided, with different layers connecting to different arrays of external contacts 61. This is schematically depicted in FIG. 6, which depicts a perspective view of part of the interposer region 60 including a first array of external contacts 61 that are connected to a conductive inner core 411 of a wire 413 of a first layer of wires 413 of a cable 410 and a second array of external contacts 61' that are connected to a conductive inner core 411' of a wire 413' of a second layer of wires 413' of the cable 410. The second layer of wires 413' may be arranged on top of the first layer of wires 413 such that the second layer of wires 413' may extend over the first array of external contacts 61, thus providing a stacked arrangement of interconnections of the IC die 128 connection cable 410, e.g. a coaxial cable. In an embodiment, part of the wires 413, 413' are coaxial wires and part of the wires 413, 413' are solid wires, i.e. wires comprising a core 411 only.

The IC die 1 may further comprise a ground pad 62 in the interposer region 60 for connecting the IC die 1 to ground, e.g. to the outer conductive sheath of a coaxial cable. The ground pad 62 may be arranged at the periphery of the interposer region 60, for example near the edge of the interposer region 60 opposite the boundary between the interposer region 60 and the sensor region 10 to facilitate the aforementioned stacked connection arrangement between the interposer region 60 and the connection cable 410. The ground pad 62 may be arranged such that the external contacts 61 are positioned in between the ground pad 62 and this boundary.

Figure 7:
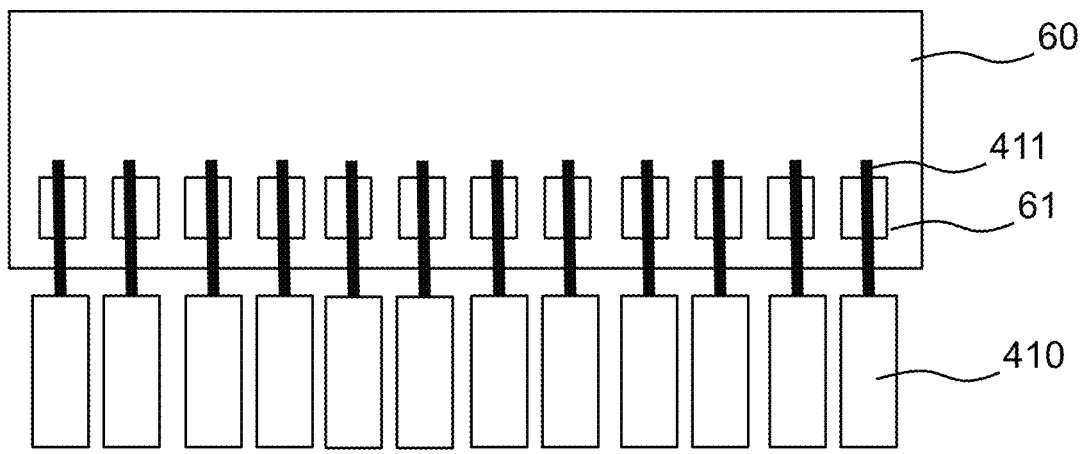
FIG. 7 schematically depicts a top view of a connection between a coaxial cable and a CMUT IC die according to an embodiment.

FIG. 7 schematically depicts a top view of the interposer region 60 including an array of external contacts 61 and a connection cable 410 comprising strip lines. The strip lines are typically stripped to expose the conductive inner core 411, with respective inner cores 411 connected to respective external contacts 61. The inner cores 411 may be connected to the external contacts 61 in any suitable manner, such as by soldering or welding. Suitable soldering techniques include the deposition of a solder on the external contacts 61 by electroplating, hot immersion or droplet deposition, with the subsequent soldering of the inner cores 411 formed by hot bar or laser reflow soldering. It is noted that the discrete passive components 320 may be mounted on the mounting pads 65 by similar connection techniques.

In an alternative embodiment, the connection cable 410 is electrically connected to the external contacts 61 by a low-temperature connection technique, e.g. epoxy bonding. This has the advantage that the risk of buildup of temperature induced stresses due to a mismatch in the thermal expansion coefficients of the different materials of the interposer region 60, e.g. metal or metal alloy contacts 61, 65 and electrically insulating materials, is avoided, thereby reducing the risk of die failures during a connection process at elevated temperatures.

In an embodiment, the array of external contacts 61 may include ground terminals. For example, the array of external contacts 61 may provide an alternating pattern of signal terminals and ground terminals, i.e. every other external contact may be a ground terminal, thereby obviating the need for a separate ground pad 62.

Figure 8:
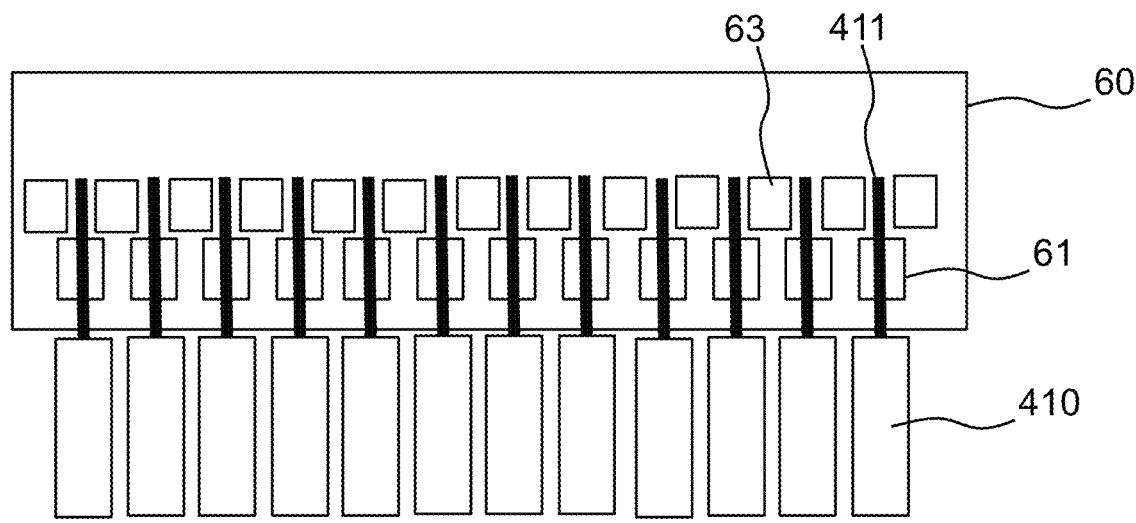
FIG. 8 schematically depicts a top view of a connection between a coaxial cable and a CMUT IC die according to another embodiment.

FIG. 8 schematically depicts a top view of a part of the interposer region 60 of an IC die 1 according to another embodiment, in which an array of external contacts 61 is accompanied by an array of alignment members 63 in between the array of external contacts 61 and the boundary between the interposer region 60 and a sensor region 10. The alignment members 63 are positioned such that each external contact 61 of the array of external contacts 61 is positioned or aligned in between a pair of neighbouring alignment members 63 in the array of alignment members 63. This is particularly advantageous when connecting the IC die 128 connection cable 410 including strip lines, where the exposed inner cores 411 of the strip lines may be guided in between neighbouring alignment members 63 in order to align such an inner core 411 with one of the external contacts 61. The alignment members 63 preferably are protrusions extending from the upper surface of the interposer region 60. Such alignment members 63 for instance may be formed by patterning an upper electrically insulating layer, e.g. the upper flexible membrane layer, e.g. a silicon nitride or silicon oxide layer, by depositing and subsequent patterning of additional dielectric layer over the interposer region 60, and so on. The alignment members 63 may have any suitable shape.

Figure 9:
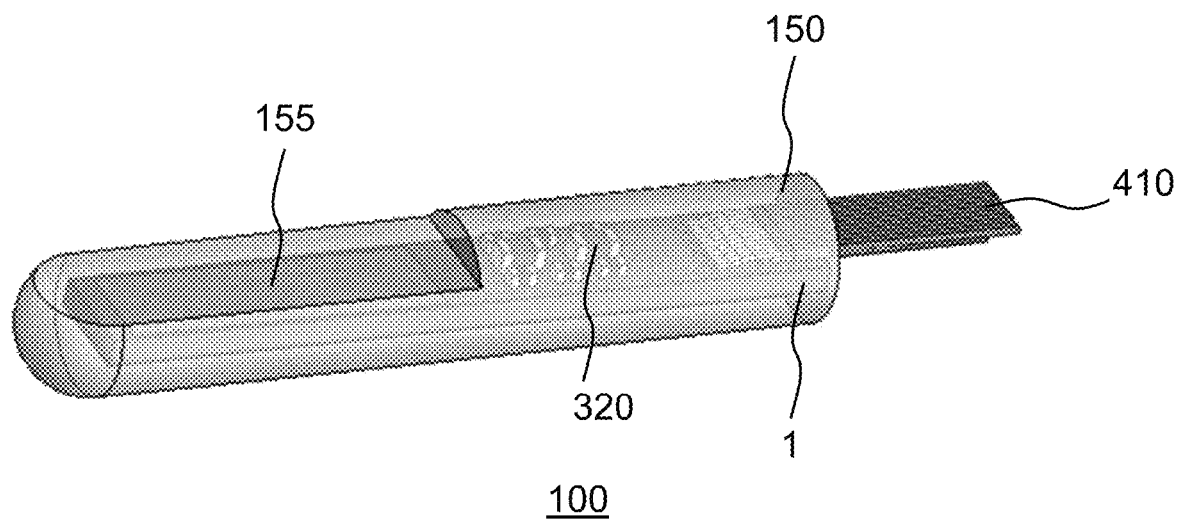
FIG. 9 schematically depicts an ultrasound probe according to an embodiment.

FIG. 9 schematically depicts an ultrasound transducer probe 100 including an embodiment of the IC die 1 connected to a connection cable 410 for connecting the IC die 1 to a control terminal of an ultrasound system. The ultrasound transducer probe 100 comprises a resin encapsulation 150 encapsulating the IC die 1 including the connections between the IC die 1 and the connection cable 410 in the interposer region 60 of the IC die 1 to protect the ultrasound transducer probe 100 from accidental damage, e.g. by reinforcing the connections between the external connections 61 and the connection cable 410. In FIG. 9, the probe 100 further comprises a number of discrete passive components 320 mounted on the mounting pads 65 of the IC die 1, which passive components 320 are also encapsulated by the resin encapsulation 150. The resin encapsulation 150 may comprise a recessed area 155 over the sensor region 10 of the IC die 1 to minimize the thickness of the resin encapsulation 150 over the sensor region 10, thereby minimizing the loss of ultrasound waves transmitted by the sensor region 10, or the loss of ultrasound echoes received by the sensor region 10 in case of a diagnostic probe 100.

Figure 10:
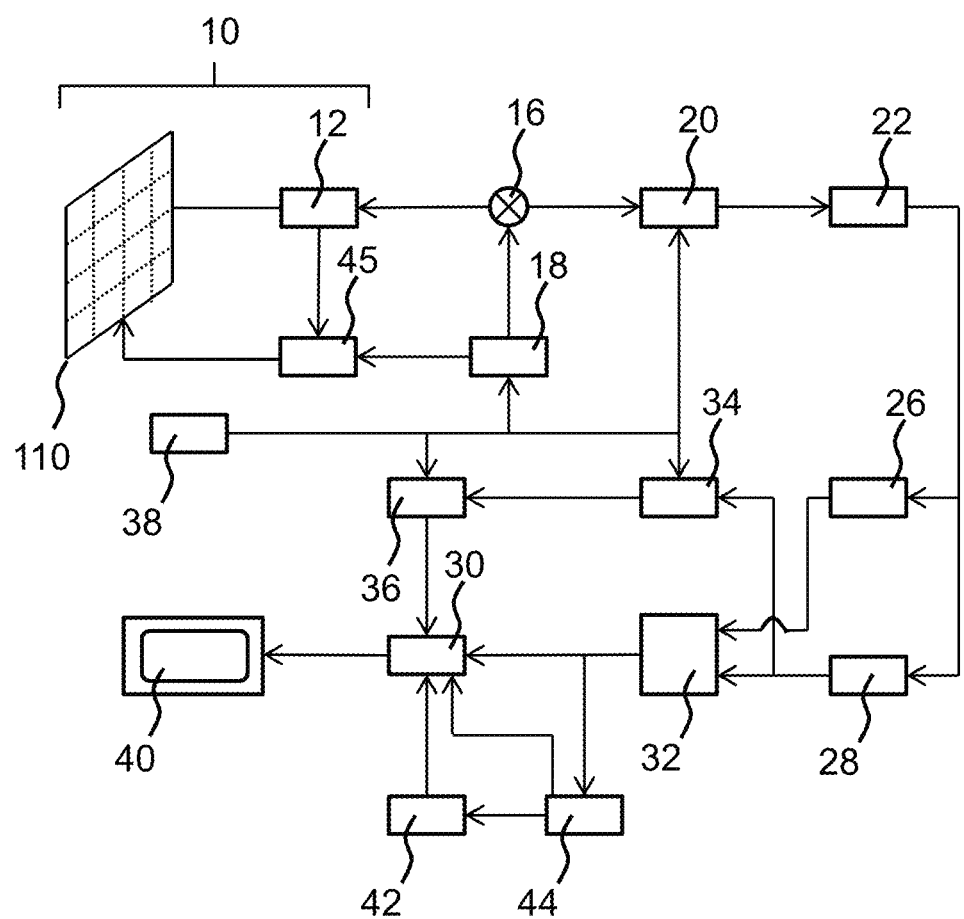
FIG. 10 schematically depicts an ultrasound system according to an example embodiment.

Referring to FIG. 10, an example embodiment of an ultrasound system with an array transducer probe 100 according to an embodiment of the present invention is shown in block diagram form. At least some of the components of the ultrasound system described below may be integrated in a control interface of such an ultrasound system as is well-known per se. Such a control interface may be coupled to the probe 100 by the connection cable 410.

In FIG. 10 an array of CMUT transducers 11 on the IC die 1 is provided as part of an ultrasound probe 100 for transmitting ultrasonic waves and optionally for receiving echo information. The transducer array may be a one- or a two-dimensional array of transducer elements capable of scanning in a 2D plane or in three dimensions for 3D imaging. The ultrasound system may be an ultrasound diagnostic imaging system, typically configured to receive echo information, or may be an ultrasound therapeutic system in which ultrasound pulses are delivered for the treatment of a particular condition, in which case the ultrasound system may not require receiver capability. In the remainder, ultrasound diagnostic imaging system will be described. The skilled person will immediately realize which integers of the ultrasound diagnostic imaging system may be omitted in an ultrasound therapeutic system.

The transducer array is coupled to a microbeam former 12 in the probe 100, e.g. mounted on the integrated interposer region 60 of the IC die 1, which controls transmission and reception of signals by the CMUT array cells or piezoelectric elements. Microbeam formers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.)

The microbeam former 12 is coupled by the probe cable, e.g. coaxial wire 410, to a transmit/receive (T/R) switch 16 which switches between transmission and reception and protects the main beam former 20 from high energy transmit signals when a microbeam former is not present or used and the transducer array is operated directly by the main system beam former 20. The transmission of ultrasonic beams from the transducer array under control of the microbeam former 12 is directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array, or at different angles for a wider field of view. The transducer controller 18 may be coupled to control a DC bias control 45 for the CMUT array. For instance, the DC bias control 45 sets DC bias voltage(s) that are applied to the CMUT cells 11 of a CMUT array.

The partially beam-formed signals produced by the microbeam former 12 are forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of CMUT transducer cells 112 (see FIG. 1-3) or piezoelectric elements. In this way the signals received by thousands of transducer elements of a transducer array can contribute efficiently to a single beam-formed signal.

The beam-formed signals are coupled to a signal processor 22. The signal processor 22 can process the received echo signals in various ways, such as band pass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The band pass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor 28 typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor 28 receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) 28 are coupled to a scan converter 32 and a multiplanar reformatter 44. The scan converter 32 arranges the echo signals in the spatial relationship from which they were received in a desired image format. For instance, the scan converter 32 may arrange the echo signal into a two dimensional (2D) sector-shaped format, or a pyramidal three dimensional (3D) image.

The scan converter 32 can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface is also coupled to the transmit controller 18 to control the generation of ultrasound signals from the transducer array and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound probe 10 may not have 3D imaging capabilities and so on. Other variations will be apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

What is claimed is:

1. An apparatus, comprising:
   an intraluminal catheter configured for insertion into a patient, wherein the intraluminal catheter comprises:
      an imaging assembly; and
      a connection cable comprising a plurality of wires,
   wherein the imaging assembly comprises:
      an integrated circuit comprising a top surface;
      a plurality of ultrasound transducers; and
      a passive component distinct from the integrated circuit and the plurality of wires,
   wherein the plurality of ultrasound transducers is disposed on a first region of the top surface, the passive component is disposed on a second region of the top surface, and the plurality of wires is coupled to the integrated circuit at the top surface such that the imaging assembly does not comprise an interposer separate from the integrated circuit,
   wherein the integrated circuit is configured to perform at least one of processing of signals received from the plurality of ultrasound transducers or generation of signals provided to the plurality of ultrasound transducers.

2. The apparatus of claim 1, wherein the integrated circuit comprises a first end and an opposite second end.

3. The apparatus of claim 2, wherein the plurality of ultrasound transducers is disposed proximate to the first end.

4. The apparatus of claim 2, wherein the plurality of wires is disposed proximate to the second end.

5. The apparatus of claim 4,
   furthering comprising a plurality of external contacts disposed on the top surface and proximate to the second end,
   wherein the plurality of wires is coupled to the plurality of external contacts.

6. The apparatus of claim 1, wherein the passive component is disposed between the plurality of ultrasound transducers and the plurality of wires.

7. The apparatus of claim 6,
   further comprising a mounting pad disposed on the top surface and between the plurality of ultrasound transducers and the plurality of wires,
   wherein the passive component is coupled to the mounting pad.

8. The apparatus of claim 1, wherein the passive component comprises a resistor, a decoupling capacitor, or a bypass capacitor.

9. The apparatus of claim 1, wherein the passive component is configured to receive power for the integrated circuit before the power is supplied to the integrated circuit.

10. The apparatus of claim 1, wherein the plurality of ultrasound transducers comprises plurality of capacitive micromachined ultrasound transducer (CMUT) cells.

11. The apparatus of claim 1, wherein the plurality of ultrasound transducers comprises a plurality of piezoelectric transducer elements.

12. The apparatus of claim 1, wherein the plurality of ultrasound transducers comprises a two-dimensional array.

* * * * *